United States Patent [19]
Shigeyasu et al.

[11] 3,970,696

[45] July 20, 1976

[54] PROCESS FOR PRODUCING AROMATIC CARBOXYLIC ACID

[75] Inventors: Motoo Shigeyasu; Michio Kuki, both of Matsuyama, Japan

[73] Assignee: Matsuyama Petrochemicals Inc., Osaka, Japan

[22] Filed: July 29, 1974

[21] Appl. No.: 492,796

[30] Foreign Application Priority Data
July 28, 1973 Japan .................................. 48-85215

[52] U.S. Cl. ............................................. 260/524 R
[51] Int. Cl.$^2$ .......................................... C07C 51/33
[58] Field of Search ................................ 260/524 R

[56] References Cited
UNITED STATES PATENTS

| | | | |
|---|---|---|---|
| 2,788,367 | 4/1957 | Bills et al. ........................... | 260/525 |
| 2,833,816 | 5/1958 | Saffer et al. ........................ | 260/524 R |
| 3,139,452 | 6/1964 | Hay .................................... | 260/524 R |

FOREIGN PATENTS OR APPLICATIONS

| | | | |
|---|---|---|---|
| 615,363 | 2/1961 | Canada ............................ | 260/524 R |

*Primary Examiner*—Anton H. Sutto
*Attorney, Agent, or Firm*—Sughrue, Rothwell, Mion, Zinn & Macpeak

[57] ABSTRACT

A process for producing an aromatic carboxylic acid by liquid-phase oxidizing an alkylbenzene with a molecular oxygen-containing gas in a lower aliphatic carboxylic acid solvent in the presence of a heavy-metal-bromine oxidation catalyst, in which the oxidation reaction is conducted using a material containing as inorganic elements only cobalt, manganese, and bromine as the catalyst components and while withdrawing from the reaction system, at least partially, the condensed liquid of a gaseous mixture discharged from the top of the reactor during the reaction and maintaining the water content of the reaction system below a definite level by introducing fresh solvent (or, preferably, the solvent recovered as a side cut fraction by distilling the condensed liquid) in an amount corresponding to the amount of the solvent withdrawn contained in the condensed liquid, and a reaction mother liquor which is formed by separating the aromatic carboxylic acid from the reaction mixture withdrawn from the reactor is recycled, as it is, to the reactor for reuse in the oxidation reaction.

10 Claims, 1 Drawing Figure

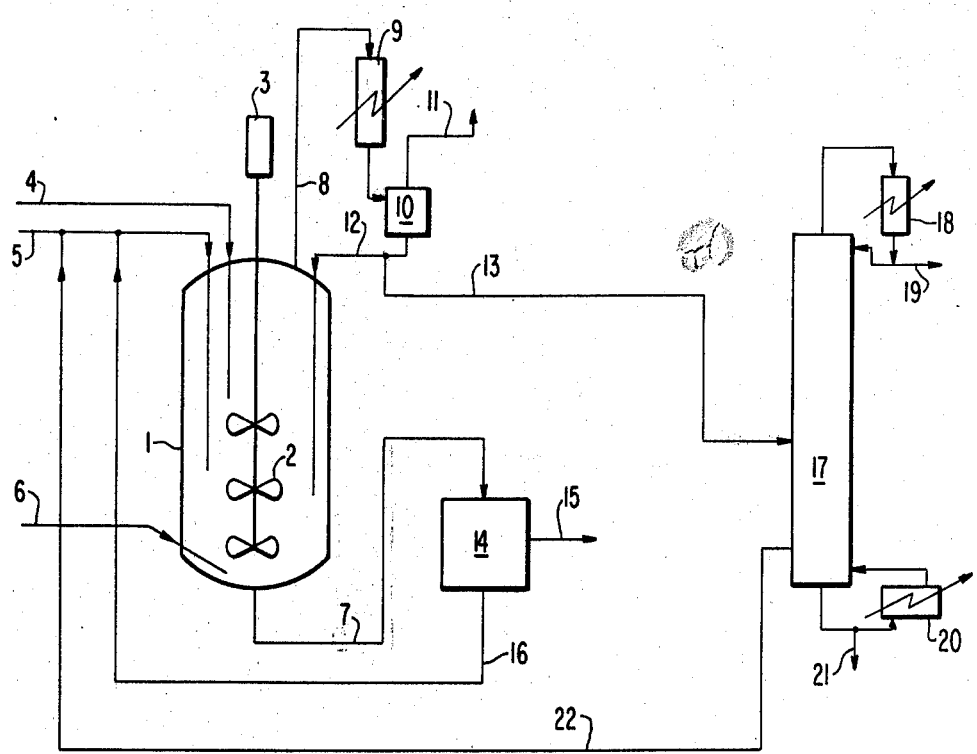

ial scale.

PROCESS FOR PRODUCING AROMATIC CARBOXYLIC ACID

BACKGROUND OF THE INVENTION

1. Field of the Invention

The present invention relates to a process for producing an aromatic carboxylic acid by the liquid-phase oxidation of alkylbenzene using oxygen. More particularly, the invention relates to a process of producing an aromatic carboxylic acid without reducing the purity and yield of the product by recycling the reaction mother liquor, as it is, formed by separating the aromatic carboxylic acid from the liquid-phase oxidation reaction product.

2. Description of the Prior Art

The process of producing an aromatic carboxylic acid by subjecting an alkylbenzene such as p-xylene to a liquid-phase oxidation with a molecular oxygen-containing gas in a lower aliphatic carboxylic acid solvent in the presence of a catalyst comprising a heavy metal such as cobalt, manganese, etc., and bromine is known as the SD process as disclosed in U.S. Pat. No. 2,833,816, and has been widely practiced on an industrial scale.

The aromatic carboxylic acid which is the desired product of the reaction is recovered from the reaction mixture obtained in the liquid-phase oxidation reaction using an ordinary separation such as filtration, precipitation, etc., and, on the other hand, the reaction mother liquor left contains almost all of the catalyst, in particular, the heavy metal catalyst used in the reaction. In this case, because the heavy metal, such as cobalt, manganese, etc., is an expensive material, to practice the oxidation reaction economically it is necessary to reuse the heavy metal catalyst effectively. For this purpose it is desirable to recycle the reaction mother liquor to the reactor for reuse as the solvent and catalyst in the subsequent reaction. However, since the reaction mother liquor contains also a large amount of water by-produced in the oxidation reaction in addition to the catalyst and solvent and if the amount of water in the reaction system is over a definite value, the oxidation reaction is greatly hindered and recycling the reaction mother liquor as it is or without removing the water therefrom is unsuitable.

Therefore, various processes have been proposed for removing water from the reaction mother liquor for recycling the reaction mother liquor to the oxidation reaction system. For example, in the process described in Japanese Patent Publication No. 5861/'69, water is removed from the reaction mother liquor, which is formed by separating terephthalic acid from the oxidation reaction product, by evaporating or distilling the reaction mother liquor at temperatures lower than 130°C. Also, in the process described in Japanese Patent Publication No. 41,339/'72, water is removed from the reaction mother liquor by distilling the reaction mother liquor in the presence of oxygen or an oxygen-containing gas. In these processes, water can be effectively removed from the reaction mother liquor. However, the reaction mother liquor obtained by separating an aromatic carboxylic acid from the oxidation reaction product contains, as is known, various organic impurities such as intermediate products and by-products from the oxidation reaction besides the solvent and water by-produced in the reaction. Hence, if the reaction mother liquor is heated to high temperatures for a long period of time to remove water therefrom by distillation as in the aforesaid conventional process, the organic impurities contained in the reaction mother liquor form polymers which are harmful to the oxidation reaction. These polymers gradually accumulate in the reaction system, while the reaction mother liquor is repeatedly used by recycling, reducing the quality of the aromatic carboxylic acid produced. Furthermore, when the reaction mother liquor is distilled by heating as stated above, harmful metallic impurities such as iron, etc., enter the reaction system due to the erosion of the distillation apparatus, etc., which also results in reducing the quality of the aromatic carboxylic acid. As described above, it is difficult in such conventional processes to avoid the accumulation of a large amount of harmful impurities in the reaction mother liquor recovered and thus the aforesaid conventional processes for removing water from the reaction mother liquor are not useful for recovering the reaction mother liquor for reuse.

SUMMARY OF THE INVENTION

As described above, since in the conventional process, in which water is removed from the reaction mother liquor by directly distilling the reaction mother liquor under heating, organic or inorganic impurities which are harmful to the oxidation reaction accumulate in the reaction system, the reduction in quality of the product aromatic carboxylic acid due to the repeated use of the reaction mother liquor is unavoidable and it has been found that in order to use repeatedly the reaction mother liquor without reducing the quality and yield of the aromatic carboxylic acid produced, it is necessary to remove water from the reaction mother liquor before reuse without employing the distillation step which forms harmful impurities as described above.

As the result of further investigations on the influences of components contained in the reaction mother liquor on the oxidation reaction, it has also been discovered that when potassium bromide and sodium bromide containing potassium and sodium, which are inorganic elements other than cobalt, manganese, and bromine, the catalyst elements used as the catalyst source, are used the inorganic elements such as potassium and sodium accumulate gradually in the reaction mother liquor when the reaction mother liquor is re-used repeatedly by recycling to the reaction system. This results in hindering the oxidation reaction and reducing the quality of the aromatic carboxylic acid as the product.

Based on the aforesaid results, various investigations were conducted and as the result thereof it has been discovered that an aromatic carboxylic acid can be produced by recycling the reaction mother liquor without reducing the quality and yield of the aromatic carboxylic acid as the product by using a material containing no harmful inorganic elements other than the catalyst elements such as cobalt, manganese, and bromine as the oxidation catalyst in a liquid-phase oxidation reaction, passing gaseous materials discharged from the reactor during the reaction through a condenser, withdrawing continuously the condensed liquid, at least partially, from the reaction system, and introducing, on the other hand, into the reaction system fresh solvent in the amount corresponding to the amount of the liquid portion withdrawn to maintain the content of water in the reaction system below a definite level.

Thus, an object of this invention is to provide an economical and simple process for producing an aromatic carboxylic acid by repeatedly using the reaction mother liquor without reducing the quality and yield of the aromatic carboxylic acid as the product in the case of producing the aromatic carboxylic acid by subjecting an alkylbenzene to a liquid-phase oxidation in a lower aliphatic carboxylic acid solvent in the presence of a heavy metal-bromine series oxidation catalyst.

Another object of this invention is to provide a process for reusing repeatedly the reaction mother liquor in the oxidation reaction without organic and inorganic impurities, which are harmful to the oxidation reaction, accumulating.

Still another object of this invention is to provide a process for reusing repeatedly the reaction mother liquor without removing water from the reaction mother liquor by a distillation, etc.

A further object of this invention is to provide a process of recovering from the condensed liquid withdrawn from the oxidation reactor the solvent in a reusable state without harmful metal impurities being present.

These and other objects of this invention will become apparent from the following descriptions.

BRIEF DESCRIPTION OF THE DRAWING

The FIGURE is a flow sheet illustrating an embodiment of the process of this invention.

DETAILED DESCRIPTION OF THE INVENTION

That is, the present invention provides a process for producing an aromatic carboxylic acid by subjecting an alkylbenzene to a liquid phase oxidation with a molecular oxygen-containing gas in a lower aliphatic carboxylic acid solvent in the presence of a heavy metal-bromine oxidation catalyst, which comprises using a material containing no inorganic elements other than the catalyst elements of cobalt, manganese, and bromine as the oxidation catalyst, condensing a gaseous mixture discharged from the top of the reactor during the progress of the reaction, withdrawing from the reaction system, at least partially, the condensed liquid mainly comprising the solvent and water formed in the oxidation reaction, introducing to the reactor, on the other hand, fresh lower aliphatic carboxylic acid solvent in an amount corresponding to the amount of the condensed liquid withdrawn to conduct the oxidation reaction at a water content below a definite level, and recycling to the oxidation reactor for reuse the reaction mother liquor, as it is, which is formed by separating the aromatic carboxylic acid from the reaction mixture from the reactor.

According to the process of this invention, water by-produced as the progress of the oxidation reaction is removed from the reaction system as a condensed liquid together with a part of the solvent during the reaction and on the other hand, fresh solvent is continuously supplied to the reaction system for compensating for the loss of the solvent withdrawn from the reaction system together with water in the condensed liquid, whereby the water content of the reaction system is always maintained at a preferable range below a definite level. Therefore, the reaction mother liquor formed by separating the product, or the aromatic carboxylic acid from the reaction mixture obtained by the liquid-phase oxidation reaction of this invention, does not contain water in such a large amount which adversely influences the oxidation reaction. Thus, in the process of this invention, the distillation treatment for removing water from the reaction mother liquor prior to the reuse of the reaction mother liquor as in the processes described in above-mentioned Japanese Patent Publication No. 5861/'69 and Japanese Patent Publication No. 41,339/'72 is unnecessary and hence the contamination of the reaction mother liquor with harmful organic impurities such as polymers formed in the case of distilling the reaction mother liquor at high temperatures and metal impurities such as iron and chromium formed by the erosion of the materials of the apparatus can be prevented.

Also, in the process of this invention, a catalyst containing cobalt, manganese, and bromine as the catalyst components is used and it is necessary to use a material which does not contain other inorganic elements adversely influencing the properties of the aromatic carboxylic acid product than these three catalyst components as the catalyst. For example, sodium bromide and potassium bromide are usually used as a source of bromine but since sodium and potassium are harmful elements in the process of this invention, the use of these compounds must be avoided. Furthermore, it is known to use heavy metals such as iron, chromium, nickel, etc., together with cobalt and manganese as catalyst components in various chemical reactions but since heavy metals other than cobalt and manganese adversely influence the oxidation reaction of an alkylbenzene and the properties of the aromatic carboxylic acid produced by the oxidation reaction, the use of such harmful heavy metals must be avoided in the process of this invention.

Also, as stated above, in the process of this invention, it is necessary for maintaining the water content of the reaction system below a definite level to condense a gaseous mixture discharged from the reactor during reaction in a condenser equipped at the top portion of the reactor, to withdraw continuously a part or all of the condensed liquid from the reaction system, and, on the other hand, to supply to the reaction system fresh solvent in an amount corresponding to the amount of the solvent withdrawn in the condensed liquid. Therefore, the lower aliphatic carboxylic acid solvent contained in the condensed liquid withdrawn from the condenser together with water is recovered by separating water therefrom and is recycled into the reaction system. In this case, water is removed from the mixture of water and the lower aliphatic carboxylic acid solvent by distilling the mixture, that is, the mixture is usually distilled in a distillation column to remove water from the top of the column and recover the solvent as the bottom fraction of the distillation column. However, when a solution containing highly corrosive components such as acetic acid and bromine as the condensed liquid in the process of this invention is distilled by heating to high temperatures for a long period of time, heavy metals such as iron and chromium which are harmful to the oxidation reaction enter the bottom fraction due to erosion of the distillation apparatus, etc. Consequently, if the solvent recovered from the bottom of the distillation column is repeatedly used as the supplemental solvent, heavy metal impurities accumulate gradually in the reaction system, which results in reducing the quality and yield of the aromatic carboxylic acid product.

Thus, as the result of investigations on developing a process for recovering the lower aliphatic carboxylic acid solvent from the condensed liquid by distilling off water therefrom without the above-mentioned difficulties, it has been discovered that the solvent can be recovered efficiently in such a state that it can be reused as it is as the solvent for the oxidation reaction without contamination by harmful heavy metal impurities by recovering the solvent as a side cut fraction and not the bottom fraction of the distillation column in the case of distilling the condensed liquid recovered from the condenser. By applying such an improved process for recovering the solvent from the condensed liquid, the solvent withdrawn from the reaction system together with water in the condensed liquid can be efficiently recovered without contamination with harmful heavy metal impurities after removing water and reused, which results in making the practice of the process for producing the aromatic carboxylic acid according to the present invention more economical.

As mentioned above, features of the process of this invention lie in the points of satisfying the following two factors;

1. the water content of the reaction system is always maintained below a definite level by withdrawing the condensed liquid and supplying fresh solvent during the progress of the oxidation reaction, and 2. the contamination of the reaction system with inorganic elements which adversely influence the oxidation reaction and the quality of the oxidation product, such as alkali metal elements, e.g., sodium and potassium, and heavy metals, e.g., iron and chromium, can be prevented.

In other words, the advantages or the objects of this invention are not obtained if any one of these factors is not satisfied.

That is, according to the process of this invention having the aforesaid features, the reaction mother liquor can be recovered without an undesirable amount of water and without harmful impurities and thus by using repeatedly the recovered reaction mother liquor, the aromatic carboxylic acid can be produced without reducing the quality and yield of the product. In particular, in the process of this invention the reaction mother liquor can be recovered in a quite harmless condition and thus the process of this invention can be very effectively applied to the production of very pure terephthalic acid for direct polymerization, the quality requirements of such a product being quite severe.

The process of this invention can be applied to the production of terephthalic acid from p-xylene as well as the production of terephthalic acid from p-di-isopropylbenzene and the production of an aromatic carboxylic acid such as benzoic acid, isophthalic acid, phthalic acid, and trimellitic acid by correspondingly oxidizing toluene, m-xylene, o-xylene, pseudocumene and other alkylbenzenes.

The most preferable catalyst used in this invention is a combination of cobalt bromide and manganese bromide, which comprises the three components of cobalt, manganese, and bromine only and does not contain other components but as the source of the bromine, free bromine, hydrobromic acid, or an organobromine compound such as 1,1,2,2-tetrabromoethane and bromoform can be used in this invention. However, as stated already, the use of sodium bromide and potassium bromide which contain inorganic elements harmful to the oxidation reaction, such as sodium and potassium, must be avoided. Other preferable examples of cobalt compounds and manganese compounds which can be used as catalyst components in this invention are cobalt acetate, manganese acetate, cobalt naphthenate, and manganese naphthenate. A suitable amount and composition of the catalyst used are as follows: (a) the amount of cobalt ranges from about 0.005 to 0.2%, preferably 0.01 to 0.15%, by weight based on the solvent, (b) the weight ratio of manganese to cobalt ranges from about 0.05:1 to 5:1, preferably 0.5:1 to 4:1, (c) the weight ratio of bromine ion to cobalt ranges from about 1:1 to 5:1, preferably 1:1 to 3.5:1. Especially in the case of producing high purity terephthalic acid in the invention, the following condition is desirable: (a) the amount of cobalt ranges from about 0.05 to 0.50%, preferably 0.08 to 0.40%, by weight based on the solvent, (b) the amount of manganese ranges from about 1 to 20%, preferably 1.5 to 13% by weight, based on the weight of cobalt, (c) the weight ratio of bromine ion to cobalt ranges from about 1.5:1 to 6.0:1, preferably 2.5:1 to 4.0:1.

Cobalt bromide and manganese bromide prepared by conventional methods can be employed in this invention. These bromides are dissolved in a proper amount of water to form an aqueous solution, mixed with the solvent and introduced into the reactor. Cobalt acetate and manganese acetate are also dissolved in the solvent and introduced into the reactor.

Examples of low aliphatic carboxylic acids which can be used as the solvent in this invention include aliphatic monocarboxylic acids having 2 to 8 carbon atoms such as acetic acid, propionic acid, and the like. In the case of producing terephthalic acid from p-xylene, the weight ratio of the solvent to p-xylene is usually greater than 2:1, and preferably is 3:1 to 6:1. As the molecular oxygen-containing gas used as the oxidizing agent in this invention, the use of air is advantageous from an economical view point. In addition to air, a gas comprising a mixture of an inert gas obtained by combustion of hydrocarbons with air or oxygen, a mixed gas of nitrogen and air, or a gas comprising a mixture of off-gas from the reactor with air or oxygen having an adequate oxygen concentration can also be used. In the case of producing terephthalic acid from p-xylene the amount of the oxygen gas to p-xylene ranges from about 3 to 500, preferably 5 to 300, mols per mol of p-xylene. The rate of the introduction of the oxygen-containing gas should be controlled so that the oxygen concentration of the off-gas from the reactor does not exceed the explosive limit, i.e., less than 8% by volume.

The reaction temperature differs depending on the kind of alkylbenzenes employed and on other reaction conditions. In the case of producing terephthalic acid from p-xylene, the reaction is generally conducted at a temperature ranging from about 80°C to 230°C, preferably 130°C to 200°C.

Because the reaction is conducted in a liquid phase, it is necessary to conduct the reaction under pressures sufficient to maintain the alkylbenzene and the solvent in the liquid state at the reaction temperature. The preferred pressure of operation ranges from about 2 to 30 kg/cm$^2$ gauge.

In the present invention it is necessary to maintain the water content of the reaction system below a definite level during the progress of the reaction. The allowable water content of the reaction system depends upon the kind of the aromatic carboxylic acid to be produced by the oxidation reaction and the quality of the product required but it is preferably as low as possible. For example, in the case of producing terephthalic acid from p-xylene, the water content of the reaction system must be less than 20% by weight, preferably less than 15% by weight. The water content of the reaction system can be maintained below a definite level by condensing a gaseous mixture mainly comprising water by-produced and the solvent used in the reaction and discharged from the top of the reactor in a condenser equipped to the reactor usually for controlling the reaction temperature, withdrawing a part or all of the condensed liquid from the condenser, and, on the other hand, supplying fresh solvent in an amount corresponding to the amount of the solvent thus withdrawn from the reaction system. The amount of the condensed liquid withdrawn from the reactor is influenced by the amount of water by-produced and the water formed by the combustion of the solvent, and is controlled so that the water content of the reaction system is maintained below a definite level. Therefore, in the case of producing terephthalic acid from p-xylene, when the water content of the reaction system is 20% by weight a minimum amount of condensed liquid is withdrawn from the reaction system. The fresh solvent thus supplied to the reaction system must have a low water content and contain no harmful inorganic impurities. Therefore, it is quite preferable to use the solvent recovered from the side cut fraction of a distillation column by distilling the condensed liquid, which is one of the features of this invention.

Also, by equipping a distiller in the outlet for the gaseous mixture at the top of the reactor, where water by-produced in the gaseous mixture can be removed as the top distillant, the concentration of the solvent of the condensed liquid is increased and the amount of the liquid withdrawn is reduced, whereby the efficiency of removing water from the reaction system can be increased.

Since in particular bromine among the catalyst components used in the oxidation reaction of this invention is consumed by the reaction, the reaction mother liquor is supplied to the reactor as a solvent-catalyst mixture in the subsequent reaction after controlling the composition of the mother liquor by supplying deficient components.

The process of this invention can be practiced as a batch system, a semi-batch system, or a continuous system.

Now, the process of this invention will be described further by reference to the embodiment illustrated in the accompanying drawing.

In the FIGURE, reactor 1 has a stirrer 2 connected to an electric motor 3 for rotating the stirrer. The reactor 1 is also equipped with inlet 4 for the raw material, the alkylbenzene, inlet 5 for the catalyst, solvent, and the reaction mother liquor, inlet 6 for an oxygen-containing gas, outlet 7 for the reaction product, outlet 8 for a gaseous mixture, and condenser 9 connected to liquid tank 10 equipped with outlet 11 for the discharged gas, conduit 12 for refluxing the condensed liquid, and conduit 13 for withdrawing the condensed liquid. Outlet 7 from the reactor is connected to separator 14 for the reaction product having outlet 15 for the product, the aromatic carboxylic acid, and conduit 16 for circulating the reaction mother liquor to the reaction. Conduit 13 attached to conduit 12 is connected to distillation column 17 for removing water from the condensed liquid having condenser 18 equipped thereto and outlet 19 for the water by-produced by the reaction at the top portion and having equipped thereto heater 20 and outlet 21 for the bottom fraction at the bottom. Also, conduit 22 for circulating recovered solvent to reactor 1 is connected to an appropriate portion (not at the bottom) of distillation column 17. In addition, in the case of equipping the distiller to the top portion of the reactor, it can be disposed above outlet 8 of the reactor.

A definite amount of solvent and catalyst is charged in reactor 1 and while stirring the reaction liquid by means of stirrer 2 equipped to the reactor, an oxygen-containing gas, e.g., air, is introduced thereto through inlet 6 and an alkylbenzene is introduced through inlet 4 to conduct the oxidation reaction of the alkylbenzene. A gaseous mixture of the exhaust gas, the evaporated solvent, and water (steam) formed in the reaction is discharged from the reactor through outlet 8 and enters condenser 9, wherein the solvent and water are condensed to form a condensed liquid. The condensed liquid and the exhaust gas are introduced into tank 10, wherein the liquid component is separated from the gaseous component. The exhaust gas thus separated is discharged from the system through conduit 11. On the other hand, a part or all of the condensed liquid is continuously withdrawn through conduit 13 for controlling the water content of the reaction system. In the case of recycling a part of the condensed liquid, it is recycled to the reactor through conduit 12.

The reaction mixture produced is withdrawn from outlet 7 and introduced into separator 14, wherein the reaction mixture is separated into the desired product, the aromatic carboxylic acid, and a reaction mother liquor. The reaction mother liquor is, as it is, recycled to reactor 1 through conduit 16 for reuse. In this case, the catalyst components such as bromine, etc., consumed in the reaction are supplied to the reaction system through conduit 5 and further fresh solvent in an amount corresponding to the amount of the solvent withdrawn from the reaction system as the condensed liquid is supplied through conduit 5.

On the other hand, the condensed liquid withdrawn from the condenser in the above reaction is sent to distillation column 17 through conduit 13 and water distilled from the top of the distillation column is condensed in condenser 18 and then withdrawn from outlet 19. The dehydrated solvent in distillation column 17 is withdrawn not as the bottom fraction but as a side cut fraction from the portion upper the bottom of the distillation column. The recovered solvent is, as it is, supplied to reactor 1 through conduit 22. Also, the bottom fraction containing heavy metal impurities, etc., is discharged from the bottom of distillation column 17.

The process of this invention will be explained further in detail by reference to the following examples. Unless otherwise indicated, all parts, percents, ratios and the like are by weight.

EXAMPLE 1

1. In a 40 liter pressure resistant reactor 1 having a titanium lining and equipped with stirrer 2 driven by stirring motor 3 at the center and a heater outside were charged 12 kg of acetic acid (having a concentration of 99.6% and an Fe content of less than 0.1 ppm), 133.3 g of cobalt bromide (hexahydrate), 5.4 g of manganese acetate, and 13.4 g of hydrobromic acid (50% aqueous solution) (the content of cobalt to acetic acid was 0.20% by weight, the content of manganese to cobalt was 5.0% by weight, and the content of the bromide ion was 3.0 times the weight of cobalt) and then p-xylene was introduced into the mixture through conduit 4 at a rate of 2 kg/hr and air was also introduced thereto through inlet 6 at a rate of 4.2 liters per gram of p-xylene for 2 hours at a reaction temperature of 190°C and a reaction pressure of 20 kg/cm². During the reaction, the condensed liquid comprising 79% by weight acetic acid and 21% by weight water recycled from tank 10 to the reactor was continuously withdrawn from a middle portion of conduit 12 at a rate of 5.0 kg/hr. The total amount of the condensed liquid thus withdrawn in the whole course of the reaction was 9.9 kg. The condensed liquid thus withdrawn was introduced to 317 L-made bubble cap plate-type dehydration column 17 having 70 plates through conduit 13 and acetic acid having a concentration of 96.8% and an Fe content of 0.3 ppm was recovered by distillation from the 70th plate. The acetic acid thus recovered was continuously sent to the reactor through conduit 22 at a rate of 5 kg/hr to maintain the level of the reaction liquid at a constant level and to control the water content of the reaction liquid.

After the introduction of p-xylene was finished, the introduction of air was stopped, the reaction mixture formed was withdrawn from outlet 7, and was separated into terephthalic acid produced and a reaction mother liquor in separator 14. The terephthalic acid thus separated was washed with acetic acid and dried. The properties and yield thereof are shown in Table 1. On the other hand, 11.6 kg of the reaction mother liquor comprising an acetic acid solution containing 10.1% by weight of water formed, 0.19% by weight of cobalt metal, 5% by weight of manganese metal to cobalt, and bromide ion of 1.7 times by weight to the amount of cobalt metal was obtained. The water content and the Fe-content of the reaction mother liquor are also shown in Table 1.

2. To 10.0 kg of the reaction mother liquor recovered in the above reaction were added 2.0 kg of acetic acid, 27.8 g of cobalt bromide, 1.1 g of manganese acetate, and 56.0 g of hydrobromic acid (50% aqueous solution) to control the composition of the reaction mother liquor. The reaction mother liquor was supplied to the reactor, and then, the condensed liquid was continuously withdrawn from the reaction system at a rate of 5.0 kg/hr as in process (1) above so that the content of water formed in the reaction system did not increase. On the other hand, the air oxidation of p-xylene was conducted while introducing continuously to the reactor acetic acid in the same amount as that of the recovered acetic acid as in process (1) above. The properties and the yield of terephthalic acid thus obtained are shown in Table 1.

The reaction mother liquor obtained was an acetic acid solution containing 9.6% by weight water formed, 0.19% by weight cobalt metal, 5% by weight manganese metal to cobalt, and bromide ion of 1.7 times by weight the amount of cobalt. The water content and the Fe-content of the reaction mother liquor are also shown in Table 1.

3. To 10 kg of the reaction mother liquor obtained above were added fresh acetic acid and catalyst components to adjust the content of cobalt metal to acetic acid to 0.20% by weight, the content of manganese metal to cobalt to 5% by weight, and the content of bromide ion to 3.0 times by weight the amount of cobalt and terephthalic acid was produced using the catalyst-solvent solution thus controlled in the same manner as in process (1) while the reaction mother liquor obtained simultaneously was recycled for reuse. The properties and the yield of terephthalic acid thus obtained and the water content and the Fe content of the reaction mother liquor are shown in Table 1.

Table 1

| | Number of Recyclings of the Reaction Mother Liquor | | | | | |
|---|---|---|---|---|---|---|
| | 0 | 1 | 2 | 5 | 15 | 20 |
| Content (ppm) of 4-Carboxybenzaldehyde | 200 | 200 | 210 | 200 | 190 | 200 |
| Molecular Extinction Coefficient* ($\epsilon_{380\,m\mu}$) | <0.01 | <0.01 | <0.01 | <0.01 | <0.01 | <0.01 |
| Color Difference** b-value | −0.4 | −0.1 | −0.2 | −0.1 | −0.3 | −0.3 |
| Yield (mol%) | 96 | 95 | 95 | 96 | 95 | 96 |
| Water Content (wt.%) of Reaction Mother Liquor | 10.1 | 9.6 | 9.8 | 9.9 | 10.1 | 9.9 |
| Fe-content (ppm) | 0.2 | 0.5 | 0.7 | 1.2 | 1.5 | 1.5 |

*The value obtained by measuring the absorption of a solution of 5 g of terephthalic acid in 100 ml of 2 N aqueous ammonia at 380 m$\mu$ using a spectrophotometer. The smaller the value, the better the hue.
**The color appearance obtained by measuring the reflected light of terephthalic acid (solid) using a color-difference meter CM-20 type made by Color Machine K.K. The b-value is a measure of yellow (+) to blue (−). The smaller the value, the better the hue.

EXAMPLE 2

Terephthalic acid was produced by employing the recycling method of the reaction mother liquor in the same manner as in Example 1 except that 1,1,2,2-tetrabromoethane was supplied to the reaction mother liquor which had not been recycled as the bromine source and fresh acetic acid having a concentration of 99.6% and an Fe content of 0.1 ppm was used as the acetic acid to be continuously supplied to the reactor for compensating for the amount of acetic acid contained in the condensed liquid withdrawn from the reactor at a rate of 5.0 kg/hour in Example 1-(2). The properties and the yield of the product, i.e., terephthalic acid and the water content and Fe-content of the reaction mother liquor formed, are shown in Table 2.

Table 2

| | Number of Recyclings of Reaction Mother Liquor | | |
|---|---|---|---|
| | 1 | 3 | 10 |
| Content (ppm) of 4-Carboxybenzaldehyde | 220 | 230 | 220 |
| Molecular Extinction Coefficient ($\epsilon_{380\,m\mu}$) | <0.01 | <0.01 | <0.01 |
| Color Difference b-value | ±0 | +0.3 | +0.2 |
| Yield (mol%) | 95 | 96 | 96 |
| Water Content (wt.%) of | 9.5 | 9.4 | 9.6 |

Table 2-continued

| | Number of Recyclings of Reaction Mother Liquor | | |
|---|---|---|---|
| | 1 | 3 | 10 |
| Reaction Mother Liquor Fe-Content (ppm) of Reaction Mother Liquor | 0.2 | 0.3 | 0.4 | the content of bromide ion became 3.0 times by weight the amount of the cobalt metal, terephthalic acid was produced by the same manner as in process (1) stated above and the reaction mother liquor obtained simultaneously was repeatedly recycled. The reaction was continued for 200 hours. During the course of the reaction, the reaction product was sampled and the properties and the yield of the terephthalic acid were measured, the results being shown in Table 3.

Table 3

| | Continuous Oxidxation Reaction Time (hr) | | | | | |
|---|---|---|---|---|---|---|
| | 2 | 10 | 20 | 50 | 100 | 200 |
| Content (ppm) of 4-Carboxybenzaldehyde | 210 | 210 | 220 | 200 | 220 | 210 |
| Molecular Extinction Coefficient ($\epsilon_{380\,m\mu}$) | <0.01 | <0.01 | <0.01 | <0.01 | <0.01 | <0.01 |
| Color Difference b-value | −0.3 | −0.3 | −0.2 | −0.3 | −0.1 | −0.3 |
| Yield (mol%) | 96 | 95 | 96 | 96 | 95 | 96 |
| Water Content (wt.%) of Reaction Mother Liquor | 9.9 | 10.0 | 10.1 | 9.8 | 10.1 | 10.0 |
| Fe Content (ppm) of Reaction Mother Liquor | 0.3 | 0.3 | 0.4 | 0.8 | 1.2 | 1.2 |

EXAMPLE 3

1. While continuing the introduction of p-xylene, the introduction of air, withdrawing of the condensed liquid, recovery of acetic acid, and the introduction of recovered acetic acid and without withdrawing the reaction product after introducing p-xylene at a rate of 2 kg/hr for 2 hours in the same procedure as in Example 1-(1), the catalyst solution supplied initially to the reactor through conduit 5, that is, an acetic acid solution containing 0.20% by weight cobalt metal, 5.0% by weight manganese metal to cobalt, and bromide ion of 3.0 times the amount of cobalt was also introduced to the reactor at a rate of 6 kg/hr to conduct a continuous run.

On the other hand, the reaction mixture was withdrawn from conduit 7 intermittently with an interval of about 10 minutes in an amount of about 1.5 kg each based on a level gage (not shown) and the reaction mixture thus withdrawn was separated into terephthalic acid and a reaction mother liquor in separator 14. The terephthalic acid thus separated was washed with acetic acid and dried. The properties and the yield of terephthalic acid are shown in Table 3.

On the other hand, the reaction mother liquor comprising an acetic acid solution containing 9.8 – 10.1% by weight of formed water, 0.19% by weight of cobalt metal, 5% by weight of manganese metal to cobalt, and bromide ion of 1.7 times by weight the amount of the cobalt metal was obtained at a rate of 5.5 – 6 kg/hr.

The water content and the Fe content of the reaction mother liquor are shown in Table 3.

2. The aforesaid continuous run was further continued for 10 hours and while continuously supplying the reaction mother liquor obtained after adding thereto fresh acetic acid and catalyst components to adjust the composition so that the content of cobalt metal to acetic acid became 0.20% by weight, the content of manganese metal to cobalt became 5% by weight, and

EXAMPLE 4 (Comparison)

Terephthalic acid was produced by employing the recycling method of the reaction mother liquor in the same way as in Example 1 except that all of the condensed liquid was recycled to the reactor without withdrawing it from the reaction system and the reaction was conducted without adjusting the water content of the reaction system. The properties and yield of terephthalic acid obtained and the water content and the Fe-content of the reaction mother liquor are shown in Table 4.

Table 4

| | Number of Recyclings of Reaction Mother Liquor | | |
|---|---|---|---|
| | 0 | 1 | 2 |
| Content (ppm) of 4-Carboxybenzaldehyde | 300 | 2400 | >50000 |
| Molecular Extinction Coefficient ($\epsilon_{380\,m\mu}$) | <0.01 | 0.03 | — |
| Color Difference b-value | +0.1 | +1.7 | +9.1 |
| Yield (mol%) | 94 | 88 | 71 |
| Water Content (wt.%) of Reaction Mother Liquor | 16.1 | 30.0 | 41.2 |
| Fe-Content (ppm) of Reaction Mother Liquor | 0.3 | 0.5 | 0.6 |

From the above results, it will be understood that since the water content of the reaction system was not adjusted, the water content increased as the number of recyclings increased, which resulted in the reduction of quality and yield of terephthalic acid.

EXAMPLE 5 (Comparison)

Terephthalic acid was produced in the same manner as in Example 1 except that sodium bromide was used in place of hydrobromic acid as the bromine source. The properties and the yield of terephthalic acid produced and the water content and the Fe-content of the reaction mother liquor are shown in Table 5.

Table 5

| | Number of Recyclings of Reaction Mother Liquor | | | | |
|---|---|---|---|---|---|
| | 0 | 1 | 2 | 3 | 5 |
| Content (ppm) of 4- | 300 | 410 | 500 | 610 | 940 |

Table 5-continued

| | Number of Recyclings of Reaction Mother Liquor | | | | |
|---|---|---|---|---|---|
| | 0 | 1 | 2 | 3 | 5 |
| Carboxybenzaldehyde Molecular Extinction Coefficient ($\epsilon_{380\,m\mu}$) | <0.01 | 0.02 | 0.04 | 0.12 | 0.18 |
| Color Difference b-value | ±0 | +0.7 | +1.9 | +3.4 | +5.0 |
| Yield (mol%) | 96 | 94 | 94 | 93 | 92 |
| Water Content (wt.%) of Reaction Mother Liquor | 9.8 | 10.1 | 9.9 | 10.1 | 9.9 |
| Fe-Content (ppm) of Reaction Mother Liquor | 0.2 | 0.5 | 0.7 | 0.9 | 1.2 |

As is clear from the above results, it will be understood that since the catalyst source contained sodium which was a harmful inorganic element, it adversely influenced the quality and yield of terephthalic acid as the result of accumulation in the reaction system.

EXAMPLE 6 (Comparison)

Terephthalic acid was produced by employing the recycling method of the reaction mother liquor in the same manner as in Example 1 except that in the case of recovering acetic acid by distilling the condensed liquid in a 317L-made bubble cap plate-type dehydration column 17, acetic acid having a concentration of 98.0% and an Fe-content of 3.1 ppm as the bottom fraction and the acetic acid was supplied to the reactor through conduit 21 and conduit 5 at a rate of 5 kg/hr in Example 1-(1). The properties and yield of terephthalic acid thus produced and the water content and Fe-content of the reaction mother liquor are shown in Table 6.

Table 6

| | Number of Recyclings of Reaction Mother Liquor | | | | |
|---|---|---|---|---|---|
| | 0 | 1 | 2 | 5 | 15 |
| Content (ppm) of 4-Carboxybenzaldehyde | 220 | 240 | 240 | 270 | 320 |
| Molecular Extinction Coefficient ($\epsilon_{380\,m\mu}$) | <0.01 | <0.01 | <0.01 | <0.01 | 0.02 |
| Color Difference b-value | −0.1 | ±0 | +0.1 | +0.3 | +0.4 |
| Yield (mol%) | 95 | 95 | 94 | 94 | 93 |
| Water Content (wt.%) of Reaction Mother Liquor | 9.8 | 9.8 | 10.2 | 11.0 | 9.9 |
| Fe-Content (ppm) of Reaction Mother Liquor | 5.0 | 8.1 | 9.5 | 15.2 | 18.2 |

As is clear from the above results, it will be understood that since acetic recovered as the bottom fraction of the dehydration column, that is, in a state contaminated with heavy metal impurities such as iron, etc., was repeatedly used, the heavy metal impurities accumulated in the reaction system, which resulted in reducing the quality and yield of terephthalic acid.

While the invention has been described in detail and wih reference to specific embodiments thereof, it will be apparent to one skilled in the art that various changes and modifications can be made therein without departing from the spirit and scope thereof.

What is claimed is:

1. In a process for producing terephthalic acid comprising liquid phase oxidizing in a reaction zone p-xylene with a molecular oxygen-containing gas in a lower aliphatic carboxylic acid solvent in the presence of an oxidation catalyst containing a heavy metal compound and a bromine compound, withdrawing from the reaction system a condensed liquid obtained by condensing a gaseous mixture discharged from the top of the reaction zone during the reaction, said condensed liquid mainly comprising the lower aliphatic carboxylic acid solvent and water formed in the reaction, distilling off water from the condensed liquid thus withdrawn in a distillation column to recover the lower aliphatic carboxylic acid solvent, introducing the recovered solvent into the reaction zone to thereby maintain the water content of the reaction system below 20% by weight and recycling to the reaction zone the reaction mother liquor as it is, said reaction mother liquor being from the reaction zone, the improvement wherein (1) the oxidation catalyst contains cobalt, manganese and bromine as the inorganic components of the catalyst and is free of other inorganic atoms or groups except hydrogen, (2) at least a part of the condensed liquid is distilled in the distillation column to thereby obtain a recovered solvent as a side cut fraction of the distillation column, (3) said recovered solvent or, if necessary, a mixture of the recovered solvent and fresh lower aliphatic carboxylic acid solvent is introduced into the reaction zone in an amount corresponding to the amount of solvent contained in the condensed liquid withdrawn from the reaction system, and (4) the entire amount of the reaction mother liquid is recycled to the reaction zone.

2. The process as claimed in claim 1, wherein the water content of the reaction system is lesss than 15% by weight.

3. The process as claimed in claim 1, wherein said lower aliphatic carboxylic acid solvent is acetic acid.

4. The process as claimed in claim 1, wherein the cobalt source of the catalyst is cobalt acetate or cobalt naphthenate.

5. The process as claimed in claim 1, wherein the manganese source of the catalyst is manganese acetate or manganese naphthenate.

6. The process as claimed in claim 1, wherein the bromine source of the catalyst is hydrogen bromide, free bromine, 1,1,2,2-tetrabromoethane, or bromoform.

7. The process as claimed in claim 1, wherein the catalyst is cobalt bromide and manganese bromide.

8. The process as claimed in claim 1, wherein said molecular oxygen-containing gas is air.

9. The process as claimed in claim 1, wherein the composition of the oxidation catalyst is (a) 0.005 to 0.2% by weight cobalt based on the weight of the solvent, (b) the weight ratio of manganese to cobalt ranges from about 0.05:1 to 5:1 and (c) the weight ratio of bromine ion to cobalt ranges from about 1:1 to 5:1.

10. The process as claimed in claim 1, wherein the composition of the oxidation catalyst is (a) 0.05 to 0.50% by weight cobalt based on the weight of the solvent, (b) 1 to 20% by weight manganese based on the weight of cobalt, and (c) the weight ratio of bromine ion to cobalt ranges from about 1.5:1 to 6.0:1.

* * * * *